US012665069B2

(12) United States Patent
Xanthis et al.

(10) Patent No.: US 12,665,069 B2
(45) Date of Patent: Jun. 23, 2026

(54) METHOD DIRECTED TO MAGNETIC RESONANCE (MR) IMAGING SIMULATION

(71) Applicant: CORSMED AB, Stockholm (SE)

(72) Inventors: Christos Xanthis, Athens (GR); Anthony Aletras, Salonika (GR); Jorge Fernandez Villena, Lisbon (PT)

(73) Assignee: CORSMED AB, Stockholm (SE)

( * ) Notice: Subject to any disclaimer, the term of this patent is extended or adjusted under 35 U.S.C. 154(b) by 395 days.

(21) Appl. No.: 18/008,294

(22) PCT Filed: Jun. 9, 2021

(86) PCT No.: PCT/SE2021/050551
§ 371 (c)(1),
(2) Date: Dec. 5, 2022

(87) PCT Pub. No.: WO2021/251885
PCT Pub. Date: Dec. 16, 2021

(65) Prior Publication Data
US 2023/0197245 A1 Jun. 22, 2023

(30) Foreign Application Priority Data

Jun. 10, 2020 (SE) .................................... 2050685-3
Sep. 18, 2020 (SE) .................................... 2051089-7

(51) Int. Cl.
*G16H 30/20* (2018.01)
*A61B 5/055* (2006.01)
*A61B 90/00* (2016.01)

(52) U.S. Cl.
CPC ............. *G16H 30/20* (2018.01); *A61B 5/055* (2013.01); *A61B 2090/3958* (2016.02)

(58) Field of Classification Search
None
See application file for complete search history.

(56) References Cited

U.S. PATENT DOCUMENTS

| | | | |
|---|---|---|---|
| 4,480,228 A | 10/1984 | Bottomley | |
| 5,374,889 A | 12/1994 | Leach et al. | |

(Continued)

FOREIGN PATENT DOCUMENTS

| | | |
|---|---|---|
| EP | 3379281 A1 | 9/2018 |
| WO | WO-2016/145355 A1 | 9/2016 |

OTHER PUBLICATIONS

Goshtasby, Ardeshir, David A. Turner, and Laurens V. Ackerman. "Matching of tomographic slices for interpolation." IEEE Transactions on Medical Imaging 11.4 (1992): 507-516. (Year: 1992).*

(Continued)

*Primary Examiner* — Michelle M Entezari Hausmann
(74) *Attorney, Agent, or Firm* — MOSER TABOADA

(57) ABSTRACT

The present invention describes method directed to magnetic resonance (MR) imaging simulation, said method comprising—creating an empty 3D slice corresponding to a prescribed slice;—placing the empty 3D slice on the transversal XY plane of an image of an anatomical model;—calculating steps of rotation and translation that if applied would bring a volume-of-interest on the transversal XY plane;—calculating steps for undoing the rotation and translation performed;—applying the steps for undoing the rotation and translation performed on the empty 3D slice so as to bring it at the position of the prescribed slice in 3D space; and—calculating interpolated values of properties of the anatomical model at points of the empty 3D slice which have been placed at the position of the prescribed slice in 3D space, preferably wherein the method also involves a subsequent step of one-to-one matching of the calculated interpolated values with the corresponding points of the empty 3D slice on the transversal XY plane before calculating the steps of rotation and translation that, if applied, would bring the volume-of-interest on the XY plane, centered at 0, 0, 0.

12 Claims, 10 Drawing Sheets

(56) References Cited

U.S. PATENT DOCUMENTS

Figures 1A, 1B:
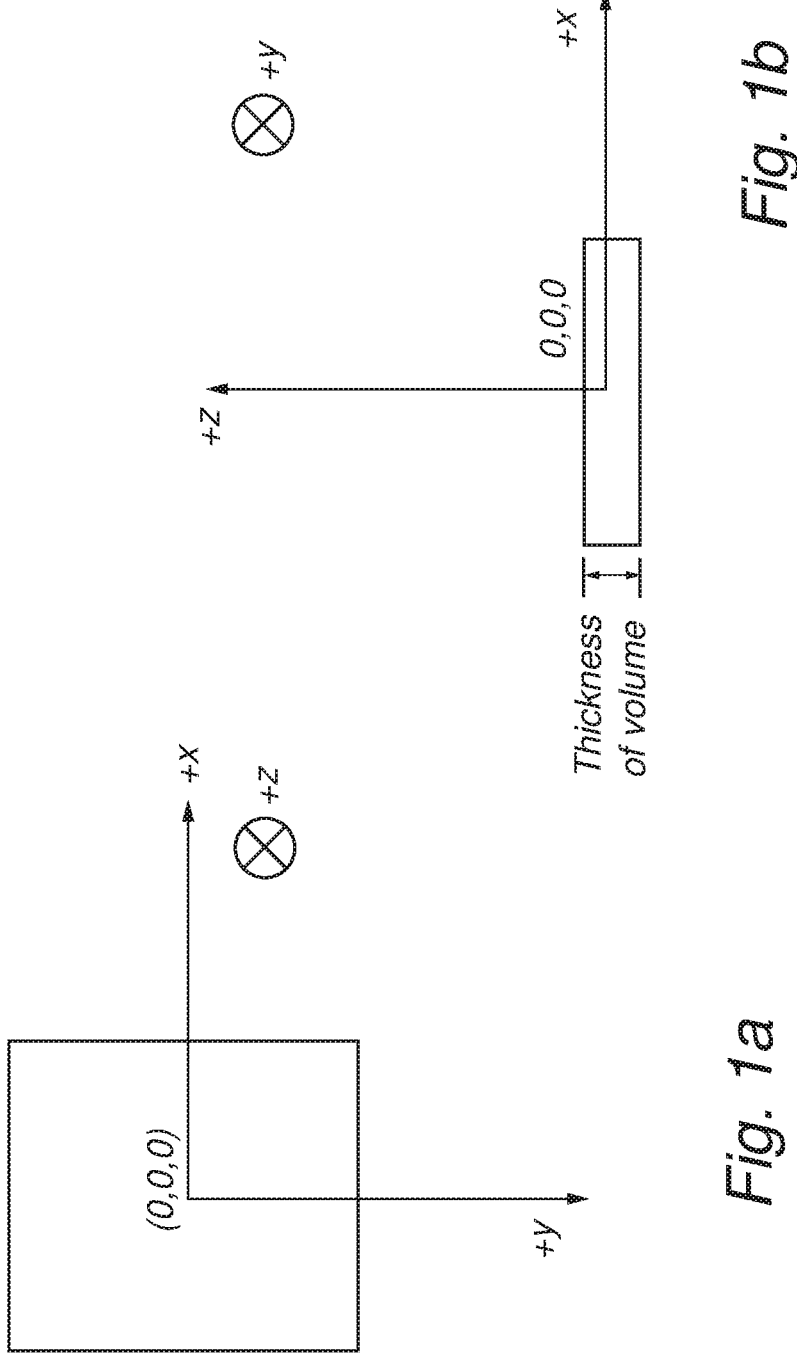

| | | | | |
|---|---|---|---|---|
| 6,122,341 | A * | 9/2000 | Butler | A61B 5/702 |
| | | | | 378/205 |
| 7,003,175 | B2 | 2/2006 | Paladini | |
| 7,319,784 | B2 | 1/2008 | Ryner et al. | |
| 9,857,443 | B2 | 1/2018 | Tadic et al. | |
| 9,933,502 | B2 | 4/2018 | Moghaddam | |
| 2006/0197780 | A1 | 9/2006 | Watkins et al. | |
| 2007/0049839 | A1 * | 3/2007 | Odry | G16H 30/40 |
| | | | | 600/529 |
| 2008/0315877 | A1 * | 12/2008 | Osman | A61B 5/055 |
| | | | | 324/309 |
| 2010/0004909 | A1 | 1/2010 | Nitz | |
| 2010/0256558 | A1 * | 10/2010 | Olson | A61B 34/77 |
| | | | | 604/95.01 |
| 2014/0056496 | A1 * | 2/2014 | Kwak | G01R 33/5611 |
| | | | | 382/131 |
| 2016/0045149 | A1 | 2/2016 | Nishimoto et al. | |
| 2016/0364878 | A1 * | 12/2016 | Guo | G02B 27/0172 |
| 2019/0197688 | A1 * | 6/2019 | Moriwaki | G06T 7/11 |
| 2019/0239926 | A1 * | 8/2019 | Pavlovskaia | A61B 17/1703 |
| 2019/0317168 | A1 * | 10/2019 | Popescu | G01R 33/56563 |
| 2020/0072930 | A1 * | 3/2020 | Zhang | G01R 33/4835 |
| 2020/0305988 | A1 * | 10/2020 | Tao | G06T 7/33 |
| 2021/0046331 | A1 * | 2/2021 | Lachaine | A61N 5/1038 |
| 2021/0259774 | A1 * | 8/2021 | Fouts | G06N 3/045 |
| 2021/0353212 | A1 * | 11/2021 | Hoshiyama | A61B 5/004 |
| 2022/0092791 | A1 * | 3/2022 | Dougherty | G06T 7/62 |

OTHER PUBLICATIONS

Klepaczko, Artur, et al. "Computer simulation of magnetic resonance angiography imaging. Parallel implementation in heterogeneous computing environment." 2012 Joint Conference New Trends in Audio & Video and Signal Processing: Algorithms, Architectures, Arrangements and Applications (NTAV/SPA). IEEE (Year: 2012).*

Blanchard, Martin, et al. "Quantitative Comparison of 3D Freehand Ultrasound and MRI Images of the Neonatal Brain." 2020 IEEE International Ultrasonics Symposium (IUS). IEEE, 2020. (Year: 2020).*

Swedish Search Report for Application No. 2050685-3 filed Jun. 10, 2020, 3 pages.

Swedish Search Report for Application No. 2051089-7 filed Sep. 18, 2020, 4 pages.

International Search Report & Written Opinion for Application No. PCT/SE2021/050551 mailed Aug. 27, 2021, 12 pages.

Xanthis, et al.; High performance MRI simulations of motion on multi-GPU systems; Journal of Cardiovascular Magnetic Resonance 2014, 16:48; http://jcmr-online.com/content/16/1/48.

Treceño-Fernández, et al.; A Web-Based Educational Magnetic Resonance Simulator: Design, Implementation and Testing; Journal of Medical Systems (2020) 44:9; https://doi.org/10.1007/s10916-019-1470-7.

Xanthis, et al.; coreMRI: A high-performance, publicly available MR simulation platform on the cloud; PLOS ONE; https://doi.org/10.1371/journal.pone.0216594; May 17, 2019.

* cited by examiner $p=T^*(r)$ $+z$ $\square\, p$ $+y$ $\square\, r$ $+x$ $(0,0,0)$

Fig. 6

*With regridding*

*With no regridding*

METHOD DIRECTED TO MAGNETIC RESONANCE (MR) IMAGING SIMULATION

FIELD OF THE INVENTION

The present invention relates to a method directed to magnetic resonance (MR) imaging simulation.

TECHNICAL BACKGROUND

The present invention is in general directed to advanced MRI simulation without the need for using a real MRI scanner. More specifically, the present invention is directed to a method for magnetic resonance (MR) imaging simulation in which a preferred computer model is used so that a certain thought volume of an object may be analyzed in an advantageous way.

SUMMARY OF THE INVENTION

The present invention refers to a method directed to magnetic resonance (MR) imaging simulation, said method comprising
    creating an empty 3D slice corresponding to a prescribed slice;
    placing the empty 3D slice on the transversal XY plane of an image of an anatomical model;
    calculating steps of rotation and translation that if applied would bring a volume-of-interest on the transversal XY plane;
    calculating steps for undoing the rotation and translation performed;
    applying the steps for undoing the rotation and translation performed on the empty 3D slice so as to bring it at the position of the prescribed slice in 3D space; and
    calculating interpolated values of properties of the anatomical model at points of the empty 3D slice which have been placed at the position of the prescribed slice in 3D space.
    In relation to the above it may be stated that an empty 3D slice is a spatially discretized volume. The empty 3D slice may be regarded as a spatially discretized field-of-view with no properties yet assigned, which corresponds to a prescribed 3D slice intended to simulate. According to the present invention, the discretized nature of the spatially discretized volume involves the structure of a 3D grid that will help to avoid potential anisotropic issues in simulations.
    Moreover, the step of calculating steps for undoing the rotation and translation performed involves a mathematical process, e.g. calculating the inverse of the total rotation which is equal to its transpose.
    Furthermore, in "coreMRI: A high-performance, publicly available MR simulation platform on the cloud", PLO-SONE, Christos G. Xanthis, Anthony H. Aletras, there is disclosed a cloud-oriented engine for advanced MRI simulations (coreMRI). The aim of the study was to develop the first advanced MR simulation platform delivered as a web service through an on-demand, scalable cloud-based and GPU-based infrastructure. As mentioned, the online MR simulation platform could be utilized as a virtual MRI scanner but also as a cloud-based, high-performance engine for advanced MR simulations in simulation-based quantitative MR (qMR) methods. In the method used, there is also performed slicing to enable the MRI simulation procedure. It should be noted that the approach suggested according to the present invention is not disclosed or hinted in this article.

SPECIFIC EMBODIMENTS OF THE INVENTION

Figure 5:
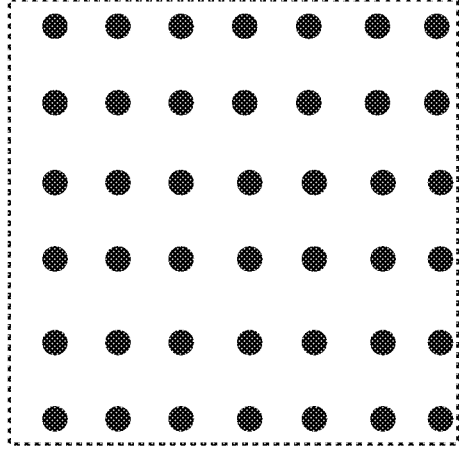
Figure 5:
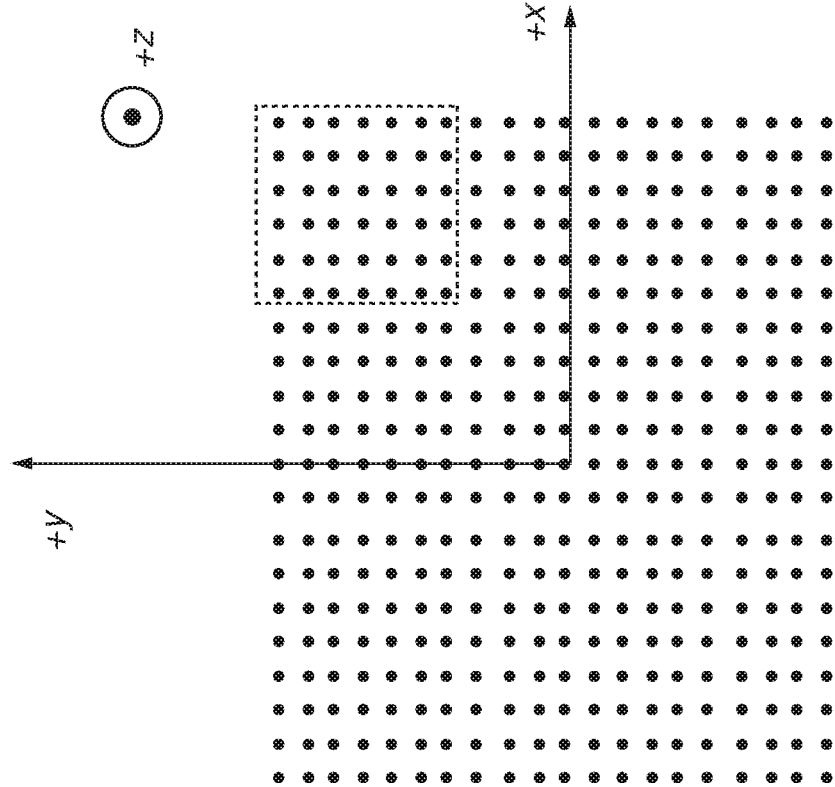

Below some specific embodiment of the present invention are provided and further described.
    According to one specific embodiment of the present invention, the step of creating an empty 3D slice corresponding to the prescribed slice involves providing an empty 3D slice of same size, with reference to field-of-view and slice thickness, as the prescribed slice.
    According to yet another embodiment, the step of placing the empty 3D slice on the transversal XY plane involves placing the empty 3D slice centered at 0, 0, 0 with the slice thickness direction along a z axis. Furthermore, according to yet another embodiment the step of calculating steps for undoing the rotation and translation performed involves calculating the steps of rotation and translation that, if applied, would bring the volume-of-interest on the XY plane, centered at 0, 0, 0.
    Moreover, according to another embodiment of the present invention, the method also involves a subsequent step of one-to-one matching of the calculated interpolated values with the corresponding points of the empty 3D slice on the transversal XY plane before calculating the steps of rotation and translation that, if applied, would bring the volume-of-interest on the XY plane, centered at 0, 0, 0.
    The method according to the present invention finds use in all types of MRI simulation. One area of special interest is in the field of imagining of human or animal bodies, e.g. for diagnostic purposes or training in this field. Therefore, according to one specific embodiment of the present invention, the method is performed based on an anatomical model representing a whole-body human or animal anatomy.
    Moreover, according to one embodiment of the present invention, the method involves removing blocks of the anatomical model that are outside the minimum and maximum coordinates of the transformed slice. In a sense, this implies that a large cube containing the full anatomical model is cropped into the smaller necessary cube enclosing the transformed slice. This may accelerate the interpolation for certain situations.
    Furthermore, the method according to the present invention may also involve obtaining the data by re-gridding in order to avoid potential anisotropic issues. This is further discussed below in relation to FIGS. 5-7. The coordinates of the target voxel in a slice in the XY plane are rotated and translated to the reference coordinates of the original anatomical model. The anatomical model suitably is gridded to perform this approach according to the present invention in a very efficient way. It should, however, be noted that this is not necessary and the method according to the present invention would work regardless. Furthermore, it may also be mentioned that the target slice coordinates are usually gridded before the rotation, but also this is not a requirement.
    As clearly stated above, the method according to the present invention is directed to the field of MRI simulation. According to one embodiment of the present invention, the method is performed in a MR scanner simulator, said method comprising
    input of data parameters into a web interface of the MR scanner simulator;
    connection of the web interface with a cloud-based simulator engine of the MR scanner simulator for transfer of data parameters to simulator engine;
    recalculation of the data parameters for the provision of one or more simulated MR signals, said recalculation being performed in the cloud;

reconstruction of an MR image based on said one or more simulated MR signals, said reconstruction of an MR image being performed in the cloud; and sending the MR image to the web interface.

According to yet another specific embodiment, the input of data parameters is at least a pulse sequence and an anatomical model. Also, other general configurations may be such input parameters. In this context it may be mentioned that a pulse sequence may be regarded as a sequence of events which change how every point in space should behave to generate a signal.

Moreover, according to yet another specific embodiment of the present invention, the simulator engine performs the recalculation and sends recalculated data to one or more GPUs (graphics processing units) of the MR scanner simulator, which GPUs send back said one or more simulated MR signals. Furthermore, according to one embodiment, the step of reconstruction of an MR image is performed by one or more CPUs (central processing units) and/or one or more GPUs (graphics processing units) of the MR scanner simulator in the cloud. As an example, MATLAB may be used for performing at least parts of the recalculation.

Furthermore, in relation to the present invention it may also be said that suitably the mathematical model used is based on the solution of the Bloch equations that describe the evolution of magnetization under the effect of RF pulsing and magnetic field.

EXPERIMENTAL EXAMPLE AND RELATED FIGURES IN THE DRAWINGS

Below there is provided an explanation of the present invention in terms of procedural implementation and also in relation to the attached figures. The information below is also provided to further explain the method according to the present invention.

According to this embodiment, the procedure may be performed according to the following:

1. Creating an empty slice (3-D grid of certain resolution) of same size (field-of-view and slice thickness) as the prescribed slice;
2. Placing this slice on the transverse plane XY, centered at 0,0,0 with the slice thickness direction along the z axis (EmptySliceOnXY);
3. Calculating the steps of rotation and translation that (if applied) would bring the volume-of-interest on the XY plane, centered at 0,0,0;
4. Calculating the steps for undoing the rotation and translation described in step 3;
5. Applying these steps (described in step 4) on the empty slice so as to bring it at the position of the prescribed slice in 3D space (EmptySliceRotated);
6. Interpolation by calculating the interpolated values of the properties of the anatomical model at the points of the empty slice that has been placed at the position of the prescribed slice in 3D space (as described in step 5); and
7. One-to-one matching of the calculated values (step 6) of points in EmptySliceRotated (step 5) to the corresponding points of EmptySliceOnXY (step 2).

In relation to the figures the following may be stated. The method according to the present invention firstly involves creating an empty slice (3-D grid of certain resolution) of same size (field-of-view and slice thickness) as the prescribed slice and placing this slice on the transverse plane XY, centered at 0,0,0 with the slice thickness direction along the z axis (orange slice in FIGS. 1a and 1b). This is shown in FIGS. 1a and 1b.

Figure 2:
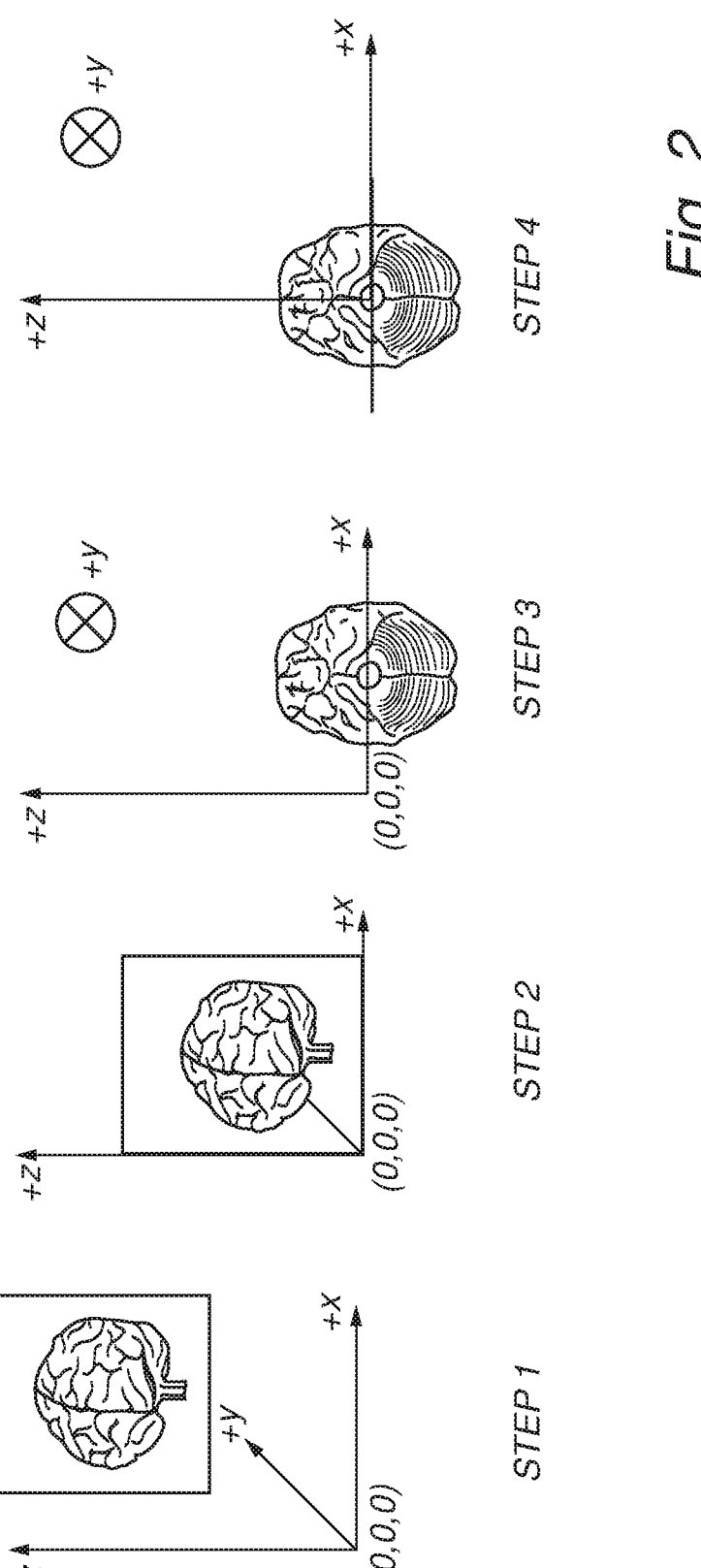
Figure 3:
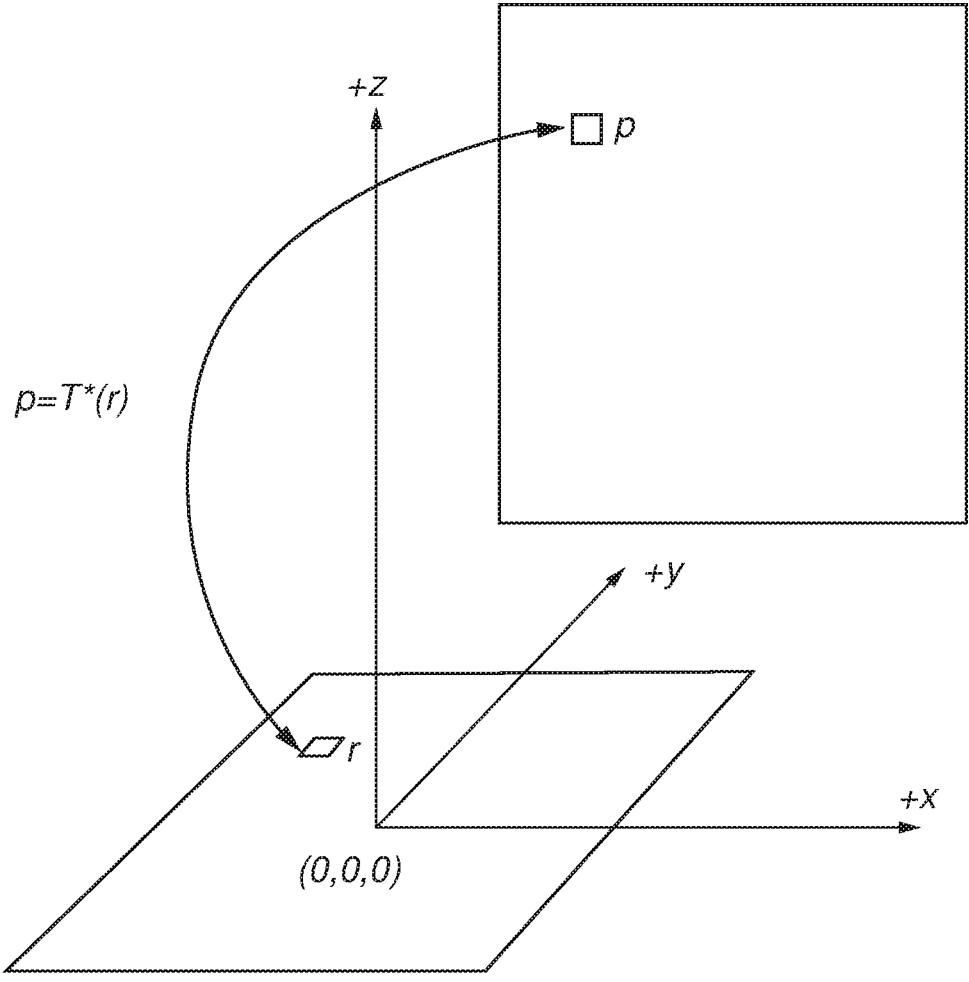

Then the method involves calculating steps of rotation and translation that if applied to the entire anatomical model would bring the volume-of-interest on the transversal XY plane, centered at 0,0,0. The sequence of events (Step 1 to Step 4 as shown in FIG. 2) will define table T shown in FIG. 3. As is visualized in FIG. 3 the method according then comprises calculating the steps for undoing the rotation and translation (table T*) and applying these steps on the empty slice (orange slice) so as to bring it at the position of the prescribed slice in 3D space (blue slice in FIG. 3).

Figure 4:
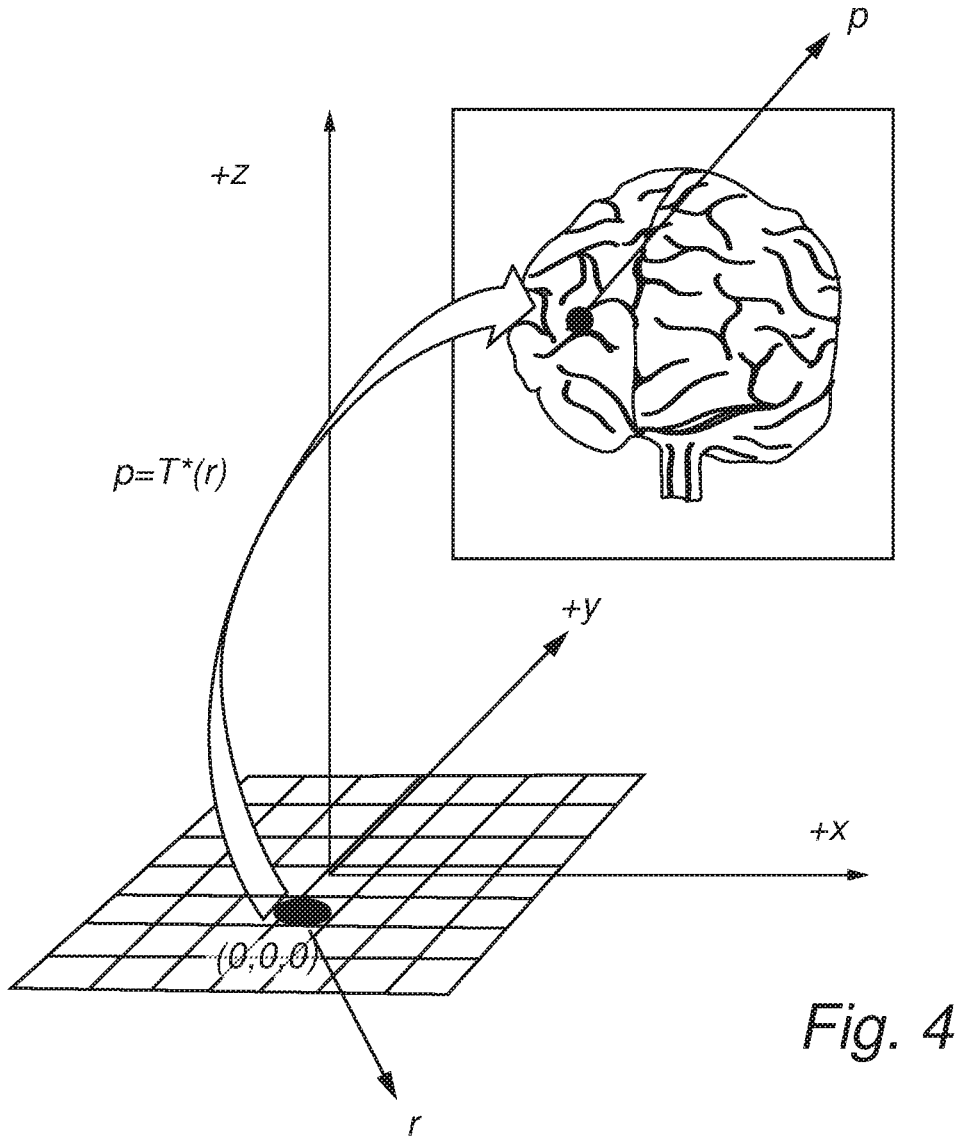

This is also visualized in FIG. 4, where a brain is also shown. In relation to FIG. 4, the following may be stated: If p=T(r) is the transformations to bring the slice of interest to a centered XY plane, and p=T*(r) the reverse (adjoint) of the transformation, the following may be considered and performed:

For each voxel with center 'r' of the empty slice (red), its equivalent properties values may be computed by:

$$value(r)=interp(T^*(r), AnatomicalModel)$$

Possible advantages for the performance include:

The number of voxels in the slice of interest is smaller than the anatomical model, and the transformation T* has to be applied less times If the "AnatomicalModel" was represented as a gridded data (structured 3D format), there is no loss of structure since no transformation is applied to the "AnatomicalModel". Therefore, a more efficient gridded interpolation can be applied.

Based on the above it may be understood that the slice of interest is the volume of interest. The slice on XY (stated as EmptySliceOnXY) now holds the properties for every point/element/spin within its volume. This slice is then the one utilized for simulation according to the present invention.

The method according to the present invention may also involve re-gridding. This is further explained below and also in relation to the FIGS. 5-7. Due to several rotational steps and rounding errors, the points of the volume of interest may not be perfectly aligned. As a result, truncation artifacts and/or spurious non-realistic echo refocusing may appear.

Figure 6:
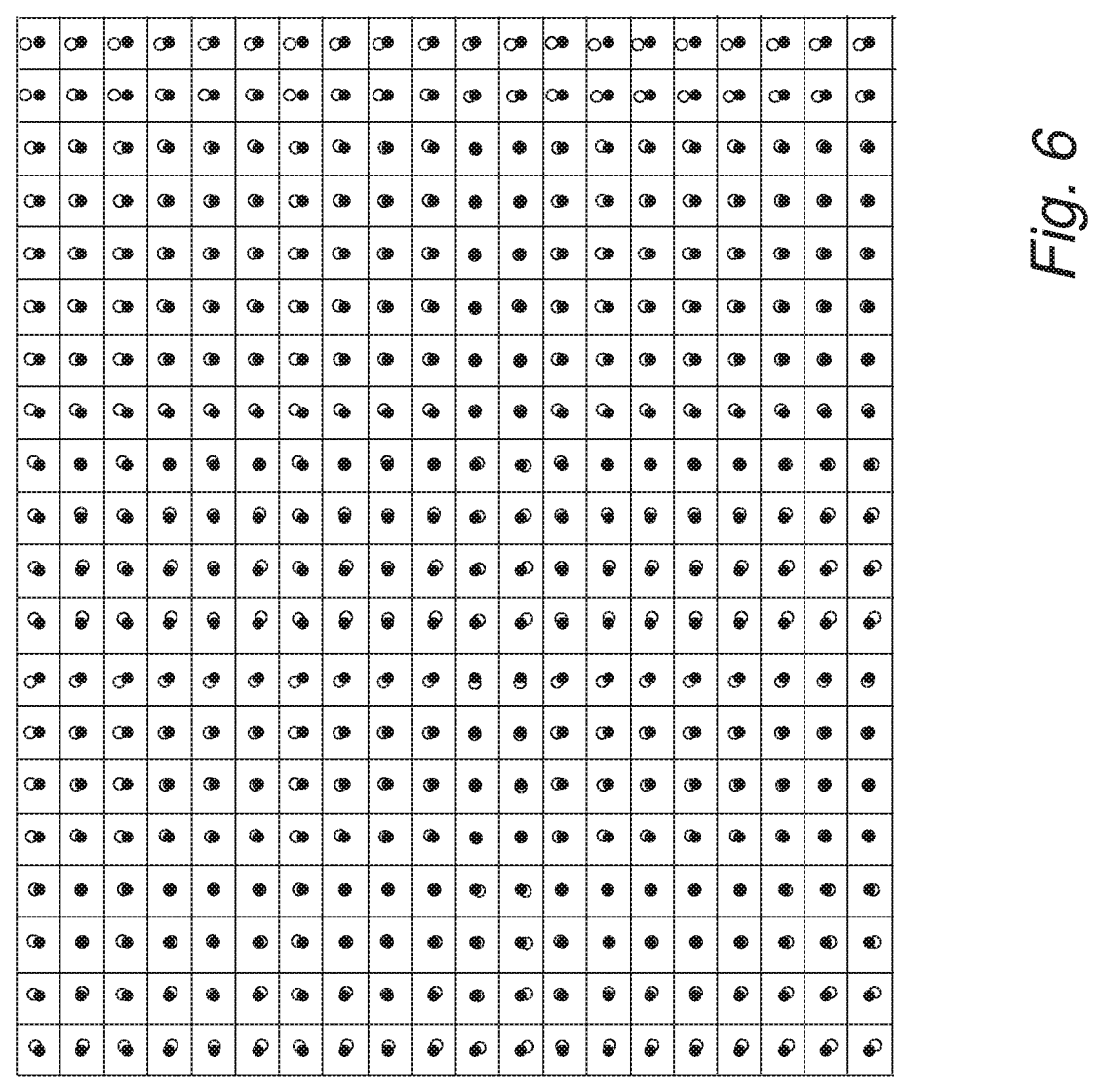
Figure 7:
Figure 7:
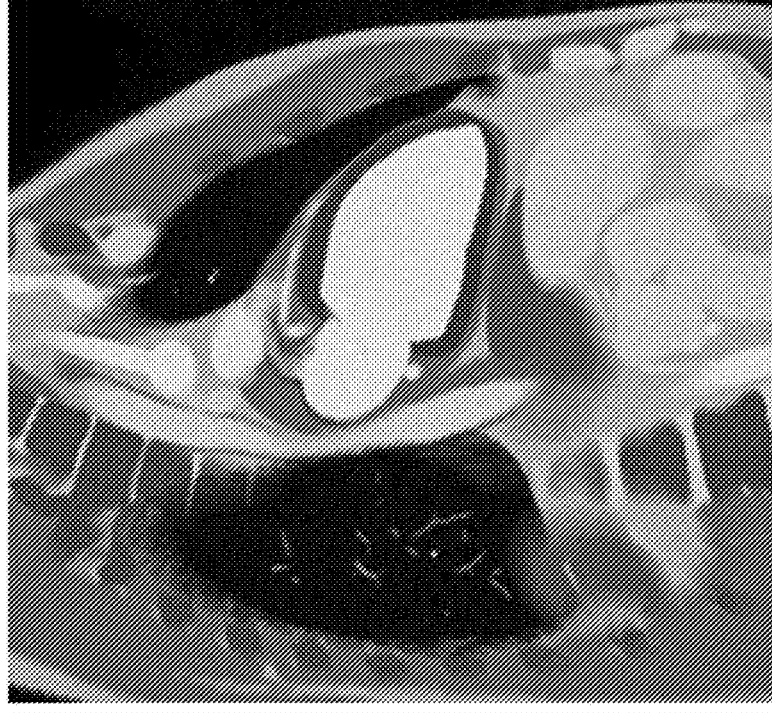
Figure 7:
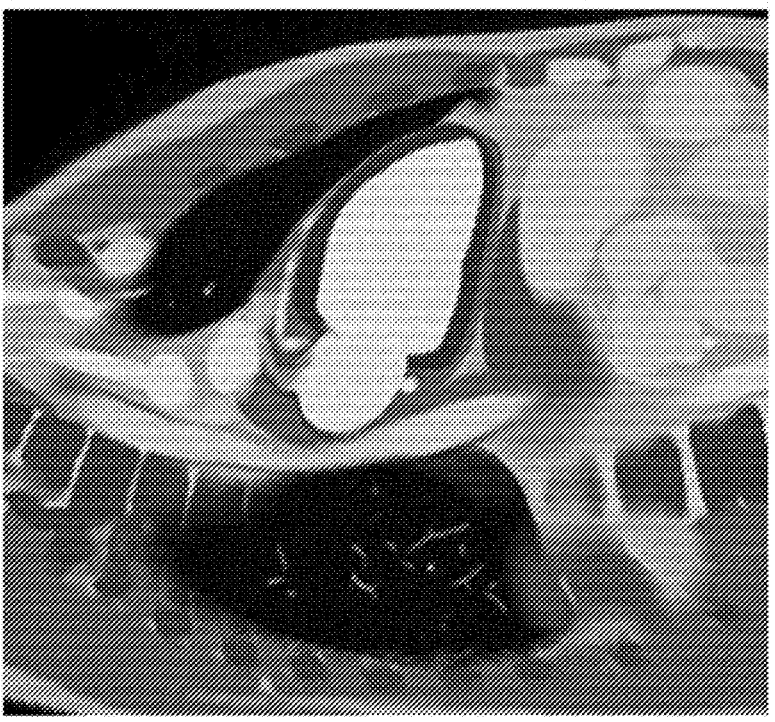

Re-gridding, remapping or interpolation of data values depending on the underlying grid means the computation method to transfer and/or calculate the data values (white dots in FIG. 6) to a new grid (black dots in FIG. 6). In FIG. 7 there is shown a result without and with re-gridding, respectively. Artificial vertical lines (left image in FIG. 7) appear in the simulated image when re-gridding is not applied on the anatomical model. The application of re-gridding improves the quality of the simulated image. The image shows a pseudo 2-chamber view of the left ventricle of the heart.

A Second Aspect of the Present Invention

Figure 8:
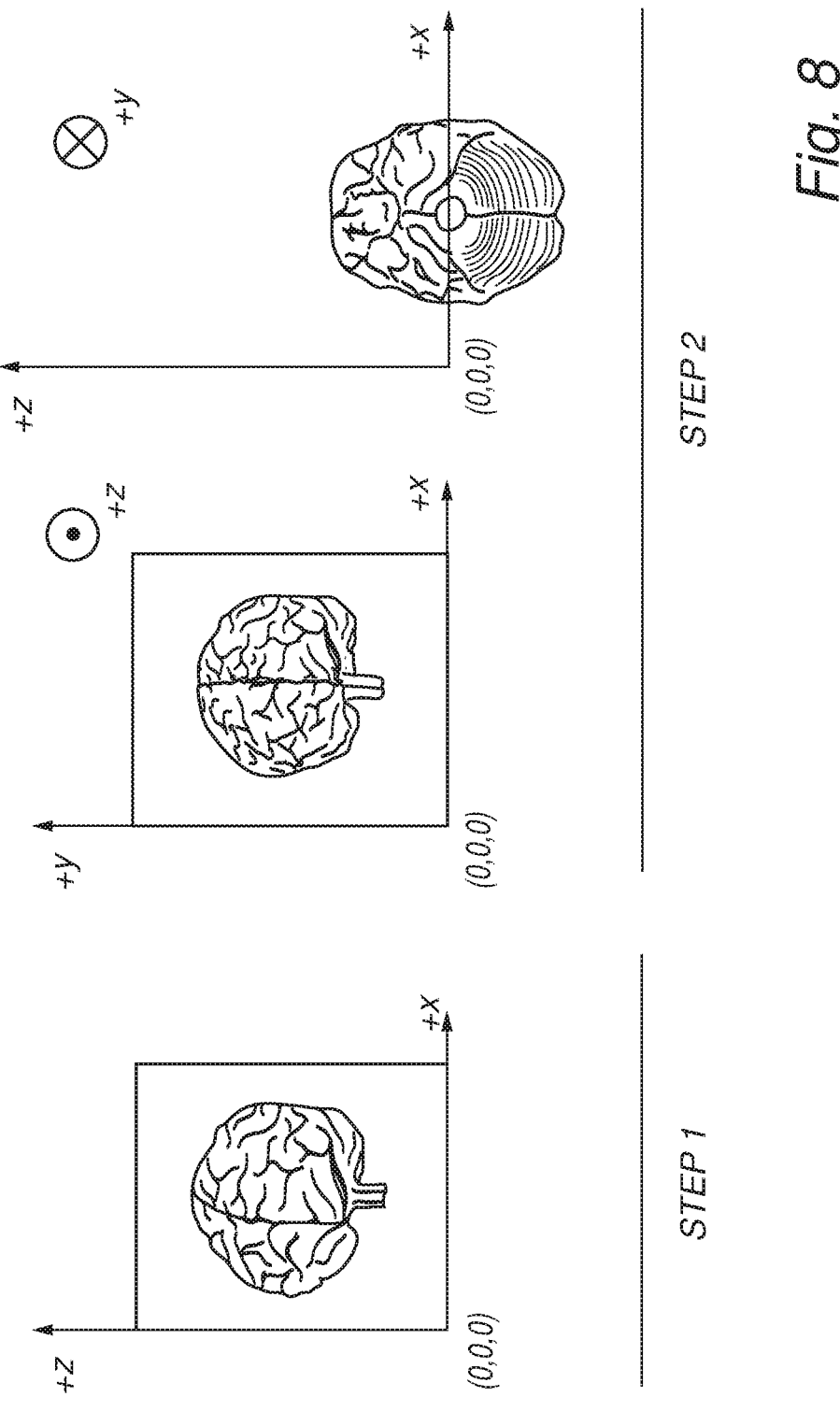
Figure 9:
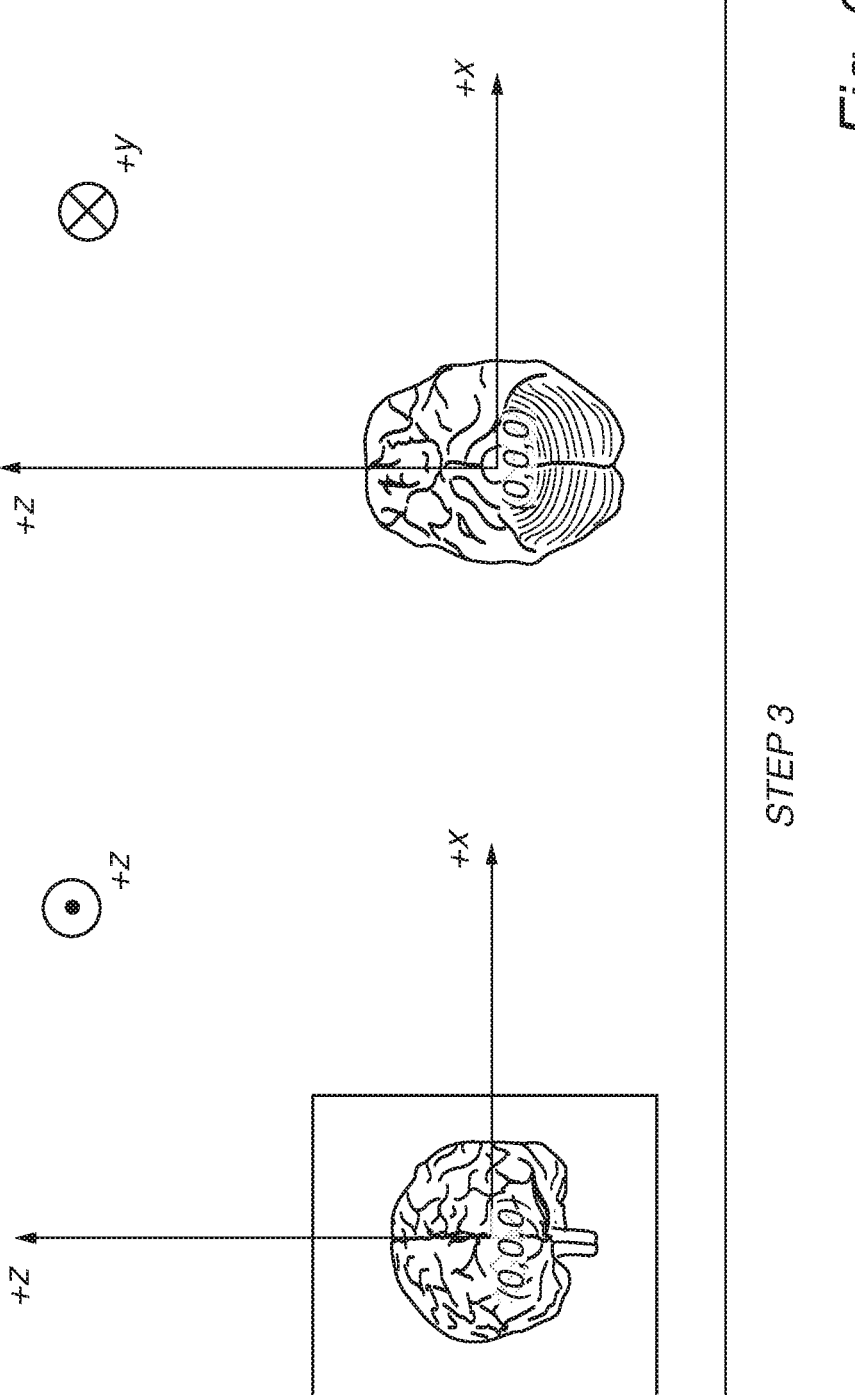
Figure 10:
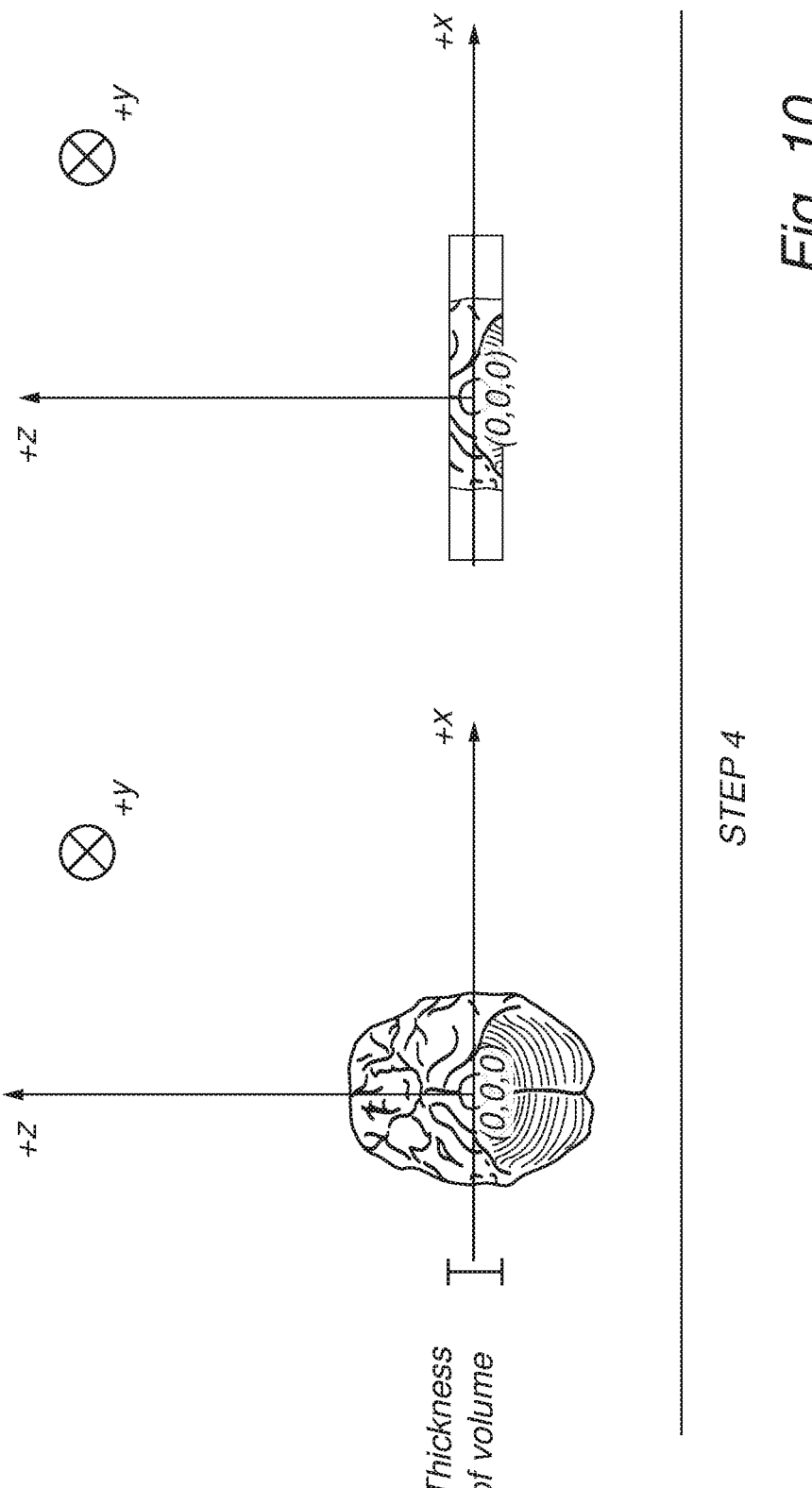

Below there is disclosed another alternative route according to the present invention. This is referred to as a second aspect of the present invention. This alternative is shown in FIGS. 8-10.

According to this second aspect, there is first intended to acquire a coronal slice of the human brain given that the patient has been placed in the scanner in a HFS (Head-First-Supine) position. The following steps are then performed. First, the next steps (see steps 1 and 2 in FIG. 8) are performed for bringing the volume-of-interest on the xy plane, vertically centered to the xy plane at z=0. A couple of steps, rotation and translation, are then applied so as to bring the volume-of-interest on the xy plane. The same steps (rotation and translation) are applied on the anatomical model as well. The number of steps to be taken depends on the initial position of the volume-of-interest in 3d space.

According to one embodiment of this second aspect, the following is performed. The first step would be to bring the volume-of-interest on the xz plane so as one of the vertices of the volume to be at the (0,0,0) point of the coordinate system. The second step would be to rotate the volume-of-interest so as to bring it on the xy plane and vertically centered to the xy plane at z=0 with the same vertex of the volume positioned at the (0,0,0) point of the coordinate system one side of the plane on the positive x axis another side of the plane on the positive y axis Furthermore, according to the example explained above, the third step would be to center the volume-of-interest at the (0,0,0) point of the coordinate system. This is depicted as step 3 in FIG. 9. The fourth step (see step 4 in FIG. 10) involves the removal of the spins/points that lie outside the thickness of the volume-of-interest. More information has been given above regarding this in relation to the simulation of slice thickness being ON and OFF.

As should be understood from above, the example provided above, also in relation to the second aspect of the present invention, and related figures, should be seen as one example of the method according to this second aspect.

Below, in "Clauses—a second aspect of the present invention" there is provided a possible embodiment of the second aspect of the present invention.

In relation to this second aspect of the present invention it should be noted that this also provides for certain embodiments of the first aspect of the present invention. Moreover, it also presents a clear introduction or definition of the problem and the goal of the present invention, such as linked to the following points:

to provide MR simulation of a slice (with thickness on or off) arbitrarily placed in a 3D anatomical model;

simulation requires bringing the slice to be centered in the XY plane;

the above is performed by setting an empty gridded slice in the XY plane, finding the adjoint of transformation T, applying it to generate the query points and interpolating in the original 3D grid with the anatomical model; and a one to one relationship between gridded positions in XY slice and the interpolated values in transformed query points allow to get information about the tissue properties.

Clauses—a Second Aspect of the Present Invention

1. A method directed to magnetic resonance (MR) imaging simulation, said method comprising rotating an anatomical model so as to bring a prescribed slice onto a transversal XY plane of an image and then removing existing spins outside of a defined slice thickness for the transversal XY plane.

2. A method directed to magnetic resonance (MR) imaging simulation, said method comprises keeping only the spins within an oblique prescribed slice and bringing the spins of the oblique prescribed slice onto a transversal XY plane of an image and then centralizing the oblique prescribed slice.

3. The method according to claim 2, wherein the method involves obtaining the spins within an oblique prescribed slice where a defined slice thickness is off, or wherein the method involves obtaining all spins within a defined slice thickness of an oblique prescribed slice, and where existing other spins are deleted.

4. The method according to any of claims 1-3, wherein the method is performed based on a 4D anatomical model representing a whole-body human or animal anatomy.

5. The method according to any of claims 1-4, wherein tissues located at positions outside a transversal position (z axis position=0) is removed so that the method performed in a computer model is performed on one or more slices with only tissues at the transversal XY plane.

6. The method according to any of claims 1-5, wherein additional spins are removed in the method performed in a computer model.

7. The method according to any of claims 1-6, wherein the method also involves re-gridding obtained data to avoid potential anisotropic issues.

8. The method according to any of claims 1-7, wherein the method is performed in a MR scanner simulator, said method comprising input of data parameters into a web interface of the MR scanner simulator;

connection of the web interface with a cloud-based simulator engine of the MR scanner simulator for transfer of data parameters to simulator engine;

recalculation of the data parameters for the provision of one or more simulated MR signals, said recalculation being performed in the cloud;

reconstruction of an MR image based on said one or more simulated MR signals, said reconstruction of an MR image being performed in the cloud; and sending the MR image to the web interface.

9. The method according to claim 8, wherein the input of data parameters is at least a pulse sequence and an anatomical model.

10. The method according to claim 8 or 9, wherein the simulator engine performs the recalculation and sends recalculated data to one or more GPUs (graphics processing units) of the MR scanner simulator, which GPUs sends back said one or more simulated MR signals.

11. The method according to any of claims 8-10, wherein the step of reconstruction of an MR image is performed by one or more CPUs (central processing units) and/or one or more GPUs (graphics processing units) of the MR scanner simulator in the cloud.

12. The method according to any of claims 8-11, wherein MATLAB is used for performing at least parts of the recalculation.

The invention claimed is:

1. A method directed to magnetic resonance (MR) imaging simulation, said method being performed only in a magnetic resonance (MR) imaging simulator, said method comprising:

creating, only in the MR imaging simulator, an empty 3D slice corresponding to a prescribed slice;

placing, only in the MR imaging simulator, the empty 3D slice on the transversal XY plane of an image of an anatomical model;

calculating, only in the MR imaging simulator, steps of rotation and translation that if applied would bring a volume-of-interest on the transversal XY plane;

calculating, only in the MR imaging simulator, steps for undoing the rotation and translation performed;

applying, only in the MR imaging simulator, the steps for undoing the rotation and translation performed on the empty 3D slice so as to bring it at the position of the prescribed slice in 3D space; and calculating, only in the MR imaging simulator, interpolated values of properties of the anatomical model at points of the empty 3D slice which have been placed at the position of the prescribed slice in 3D space.

2. The method according to claim 1, wherein the step of creating an empty 3D slice corresponding to the prescribed slice involves providing an empty 3D slice of same size, with reference to field-of-view and slice thickness, as the prescribed slice.

3. The method according to claim 1, wherein the step of placing the empty 3D slice on the transversal XY plane involves placing the empty 3D slice centered at 0, 0, 0 with the slice thickness direction along a z axis.

4. The method according to claim 1, wherein the step of calculating steps for undoing the rotation and translation performed involves calculating the steps of rotation and translation that, if applied, would bring the volume-of-interest on the XY plane, centered at 0, 0, 0.

5. The method according to claim 4, wherein the method also involves a subsequent step of one-to-one matching of the calculated interpolated values with the corresponding points of the empty 3D slice on the transversal XY plane before calculating the steps of rotation and translation that, if applied, would bring the volume-of-interest on the XY plane, centered at 0, 0, 0.

6. The method according to claim 1, wherein the method is performed based on an anatomical model representing a whole-body human or animal anatomy.

7. The method according to claim 1, wherein the method involves removing blocks of the anatomical model that are outside the minimum and maximum coordinates of the transformed slice.

8. The method according to claim 1, wherein the method also involves obtaining the data by re-gridding in order to avoid potential anisotropic issues.

9. The method according to claim 1, wherein the method is performed in a MR scanner simulator, said method comprising input of data parameters into a web interface of the MR scanner simulator;

connection of the web interface with a cloud-based simulator engine of the MR scanner simulator for transfer of data parameters to simulator engine;

recalculation of the data parameters for the provision of one or more simulated MR signals, said recalculation being performed in the cloud;

reconstruction of an MR image based on said one or more simulated MR signals, said reconstruction of an MR image being performed in the cloud; and sending the MR image to the web interface.

10. The method according to claim 9, wherein the input of data parameters is at least a pulse sequence and an anatomical model.

11. The method according to claim 9, wherein the simulator engine performs the recalculation and sends recalculated data to one or more GPUs (graphics processing units) of the MR scanner simulator, which GPUs sends back said one or more simulated MR signals.

12. The method according to claim 9, wherein the step of reconstruction of an MR image is performed by one or more CPUs (central processing units) and/or one or more GPUs (graphics processing units) of the MR scanner simulator in the cloud.

* * * * *